United States Patent
Stone

(10) Patent No.: US 10,314,517 B2
(45) Date of Patent: Jun. 11, 2019

(54) RESPIRATION MONITORING SYSTEM AND METHOD

(71) Applicant: Medical Design Solutions, Inc., Milpitas, CA (US)

(72) Inventor: Robert T Stone, Sunnyvale, CA (US)

(73) Assignee: Medical Design Solutions, Inc., Milpitas, CA (US)

(*) Notice: Subject to any disclaimer, the term of this patent is extended or adjusted under 35 U.S.C. 154(b) by 0 days.

(21) Appl. No.: 16/117,921

(22) Filed: Aug. 30, 2018

(65) Prior Publication Data

US 2018/0368732 A1 Dec. 27, 2018

Related U.S. Application Data

(63) Continuation of application No. 15/133,497, filed on Apr. 20, 2016, now Pat. No. 10,064,570, and a continuation-in-part of application No. 13/854,280, filed on Apr. 1, 2013, now abandoned.

(51) Int. Cl.
| | |
|---|---|
| *A61B 5/08* | (2006.01) |
| *A61B 5/091* | (2006.01) |
| *A61B 5/00* | (2006.01) |
| *A61B 5/01* | (2006.01) |
| *A61B 5/113* | (2006.01) |
| *A61B 5/0205* | (2006.01) |

(52) U.S. Cl.
CPC .............. *A61B 5/091* (2013.01); *A61B 5/01* (2013.01); *A61B 5/08* (2013.01); *A61B 5/1135* (2013.01); *A61B 5/6804* (2013.01); *A61B 5/6805* (2013.01); *A61B 5/6831* (2013.01); *A61B 5/7257* (2013.01); *A61B 5/742* (2013.01); *A61B 5/02055* (2013.01); *A61B 2562/0223* (2013.01)

(58) Field of Classification Search
CPC .. A61B 5/091; A61B 5/00; A61B 5/01; A61B 5/742; A61B 5/7257; A61B 5/6804; A61B 5/08; A61B 5/1135; A61B 5/6805; A61B 5/6831; A61B 2562/0223; A61B 5/02055
See application file for complete search history.

(56) References Cited

U.S. PATENT DOCUMENTS

| | | | |
|---|---|---|---|
| 2002/0032386 A1* | 3/2002 | Sackner | A61B 5/0205 600/536 |
| 2008/0255468 A1* | 10/2008 | Derchak | A61B 5/0205 600/529 |
| 2011/0054271 A1* | 3/2011 | Derchak | A61B 5/0002 600/301 |
| 2016/0228038 A1* | 8/2016 | Stone | A61B 5/091 |

\* cited by examiner

*Primary Examiner* — Eric J Messersmith
(74) *Attorney, Agent, or Firm* — Francis Law Group

(57) ABSTRACT

A wearable respiration monitoring system and associated method that is configured to (i) determine three dimensional displacement of the spine of a subject with respect to the axial displacement of the subject's chest wall, (ii) process the three dimensional anatomical data, (iii) determine at least one respiration parameter associated with the monitored subject as a function of the three dimensional anatomical data, and (iv) generate at least one respiration parameter signal representing the respiration parameter.

2 Claims, 6 Drawing Sheets

RESPIRATION MONITORING SYSTEM AND METHOD

CROSS-REFERENCES TO RELATED APPLICATIONS

This application is a continuation of U.S. application Ser. No. 15/133,497, filed on Apr. 20, 2016, which is a continuation-in-part of U.S. application Ser. No. 13/854,280, filed on Apr. 1, 2013.

FIELD OF THE INVENTION

The present invention relates to systems and methods for monitoring physiological characteristics of a subject. More particularly, the present invention relates to apparatus, systems and methods for determining a plurality of physiological characteristics; particularly, respiratory characteristics, in real time.

BACKGROUND OF THE INVENTION

In medical diagnosis and treatment of a subject, it is often necessary to assess one or more physiological characteristics; particularly, respiratory characteristics. A key respiratory characteristic is respiratory air volume (or tidal volume).

Various conventional methods and systems have thus been employed to measure (or determine) tidal volume. One method includes having the patient or subject breathe into a mouthpiece connected to a flow rate measuring device. Flow rate is then integrated to provide air volume change.

As is well known in the art, there are several drawbacks and disadvantages associated with employing a mouthpiece. A significant drawback associated with a mouthpiece and nose-clip measuring device is that the noted items cause changes in the monitored subject's respiratory pattern (i.e. rate and volume). Tidal volume determinations based on a mouthpiece and nose-clip are, thus, often inaccurate.

Other conventional devices for determining tidal volume include respiration monitors. Illustrative are the systems disclosed in U.S. Pat. Nos. 3,831,586 and 4,033,332.

Although the noted systems eliminate many of the disadvantages associated with a mouthpiece, the systems do not, in general, provide an accurate measurement of tidal volume. Further, the systems are typically only used to signal an attendant when a subject's breathing activity changes sharply or stops.

A further means for determining tidal volume is to measure the change in size (or displacement) of the rib cage and abdomen, as it is well known that lung volume is a function of these two parameters. A number of systems and devices have been employed to measure the change in size (i.e. circumference) of the rib cage (and/or abdomen), including pneumobelts and respiratory inductive plethysmograph (RIP) belts.

RIP belts are a common means employed to measure changes in the cross-sectional areas of the rib cage and abdomen. RIP belts include conductive loops of wire that are coiled and sewed into an elastic belt. As the coil stretches and contracts in response to changes in a subject's chest cavity size, a magnetic field generated by the wire changes. The output voltage of an RIP belt is generally related to changes in the expanded length of the belt and, thus, changes in the enclosed cross-sectional area.

In practice, measuring changes in the cross-sectional areas of the abdomen can increase the accuracy of RIP belt systems. To measure changes in the cross-sectional areas of the rib cage and abdomen, one belt is typically secured around the mid-thorax and a second belt is typically placed around the mid-abdomen.

RIP belts can also be embedded in a garment, such as a shirt or vest, and appropriately positioned therein to measure rib cage and abdominal displacements, and other anatomical and physiological parameters. Illustrative is the system disclosed in U.S. Pat. No. 6,551,252.

There are, however, several drawbacks associated with most RIP belt systems. A major drawback is that RIP belts are typically expensive in terms of material construction and in terms of the electrical and computing power required to operate them.

In an attempt to rectify the drawbacks associated with RIP belt systems, various magnetometer-based systems have been recently developed to measure displacements of the rib cage and abdomen and, thereby, various respiratory parameters. The noted magnetometer-based systems typically comprise at least one pair of tuned air-core magnetometers or electromagnetic coils. The paired magnetometers are responsive to changes in a spaced distance therebetween; the changes being reflected in the difference between the strength of the magnetic field between the paired magnetometers.

To measure changes in (or displacement of) the anteroposterior diameter of the rib cage, a first magnetometer is typically placed over the sternum at the level proximate the 4th intercostal space and the second magnetometer is placed over the spine at the same level.

In some magnetometer-based systems, additional magnetometers are employed to increase the accuracy of the system. For example, to measure changes in the anteroposterior diameter of the abdomen, a third magnetometer can be placed on the abdomen at the level of the umbilicus and a fourth magnetometer can be placed over the spine at the same level. Illustrative is the magnetometer-based system disclosed in U.S. Pub. No. 2011/0054271.

Over the operational range of distances, the output voltage is linearly related to the distance between two magnetometers; provided, the axes of the magnetometers remain substantially parallel to each other. As rotation of the axes can change the voltage, the magnetometers are typically secured to the subject's skin in a parallel fashion, whereby rotation due to the motion of underlying soft tissue is minimized.

To overcome the problems associated with direct attachment of magnetometers to the skin of a subject, some magnetometer-based systems are configured to embed or carry the magnetometers (and associated physiological sensors) in a wearable garment, such as a shirt or vest. The wearable monitoring garment also facilitates repeated and convenient positioning of magnetometers at virtually any appropriate (or desired) position on a subject's torso.

A major drawback and disadvantage associated with many garment based magnetometer systems is that the wires that are employed to effectuate communication by and between the magnetometers and other electronic components, e.g., sensors, are typically disposed outside of the garment or disposed partially or wholly within the garment seams. As a result, the wires can, and often will, catch and tangle on objects. The wires also reduce mobility and add weight. Further, the wires are not, in general, washable or resistant to corrosion. Such a design is, thus, not very robust.

In an effort to overcome the drawbacks associated with exposed wires, various systems have been developed that employ conductive garment fabrics, wherein electronic circuits and/or data and power conductors are integrated within the garment itself. Illustrative are the garment based systems disclosed in U.S. Pat. Nos. 6,080,690 and 5,906,004.

There are, however, several drawbacks associated with such systems. For example, routing of the data or power between electronic components is limited without extensive formation of electrical junctions in the fabric—a very cumbersome manufacturing process. In addition, such garments are also uncomfortable and cannot withstand repeated wash cycles.

A further drawback and disadvantage of systems employing conductive garment fabrics, as well as exposed wiring, is that it is difficult to achieve an effective or secure mechanical and electrical interconnection between external or portable modules or sub-systems, e.g., processing or control unit, and the integrated circuitry and/or electronic components.

It would thus be desirable to provide a respiration monitoring system and method that (i) accurately measures one or more respiration parameters or characteristics associated with a user or wearer, (ii) does not require the user to secure electrodes to their body or to use any conductive gels, (iii) does not include any exposed electrical circuitry, (iv) does not include any wires that must be connected or routed by the wearer, (v) does not interfere with the activities of or duties carried out by the user, and (vi) is aesthetically pleasing.

It is therefore an object of the present invention to provide a respiration monitoring system and method that accurately (i) determines three dimensional displacement of the spine of a subject (or wearer of a monitoring system) with respect to the axial displacement of the subject's chest wall, (ii) process the three dimensional anatomical data, (iii) determine at least one respiration parameter associated with the monitored subject as a function of the three dimensional anatomical data, and (iv) generate at least one respiration parameter signal representing the respiration parameter.

It is another object of the present invention to provide a respiration monitoring system and method that accurately measures multiple respiration parameters associated with a user or wearer, while minimizing inference from external sources, such as electromagnetic radiation.

It is another object of the present invention to provide a respiration monitoring system and method that does not require the user to secure electrodes to his/her body or to use any conductive gels.

It is another object of the present invention to provide a respiration monitoring system and method that does not include any exposed electrical circuitry.

It is another object of the present invention to provide a respiration monitoring system and method that does not include any wires that must be connected or routed by the wearer.

It is another object of the present invention to provide a respiration monitoring system and method that includes reliable and effective means to connect external modules, e.g. processing units.

It is another object of the present invention to provide a respiration monitoring system and method that does not interfere with the activities of or duties carried out by the user.

SUMMARY OF THE INVENTION

The present invention is directed to a respiration monitoring system and associated method that is configured to (i) determine three dimensional displacement of the spine of a subject with respect to the axial displacement of the subject's chest wall, (ii) process the three dimensional anatomical data, (iii) determine at least one respiration parameter associated with the monitored subject as a function of the three dimensional anatomical data, and (iv) generate at least one respiration parameter signal representing the respiration parameter.

In a preferred embodiment of the invention, the system includes a garment that is configured to cover at least the chest region and upper back of a wearer (or user). The garment includes a circumferential band having a respiration detection system and integral signal transmission means associated therewith.

In some embodiments, the system further includes one or more additional physiological sensors that are in communication with the signal transmission means.

In a preferred embodiment of the invention, the respiration monitoring system includes at least one permanent magnet and at least one electromagnetic coil or magnetometer that are configured and positioned to detect three dimensional displacements of the spine with respect to axial displacements of the chest wall of the user.

In a preferred embodiment of the invention, the respiration monitoring system further includes an electronics module that is in communication with the respiration detection system.

In a preferred embodiment, the electronics module includes at least a processing system and data transmission system.

In a preferred embodiment, the module processing system includes programs, parameters, instructions and at least one algorithm to control the respiration detection system and the function thereof, and the transmission and receipt of signals therefrom.

The module processing system is also preferably programmed and configured to (i) receive and process three dimensional anatomical data, i.e. anatomical displacement signals representing same, from the respiration detection system, (ii) process the anatomical displacement signals, (iii) determine at least one respiration parameter associated with the monitored subject as a function of the anatomical displacement signals, and (iv) generate at least one respiration parameter signal representing the respiration parameter.

In some embodiments, the monitoring system further includes a remote display unit having a receiver that is programmed and configured to receive the transmitted respiration parameter signals. The remote display is also programmed to display respiration parameters associated with the respiration parameter signals on the display unit.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
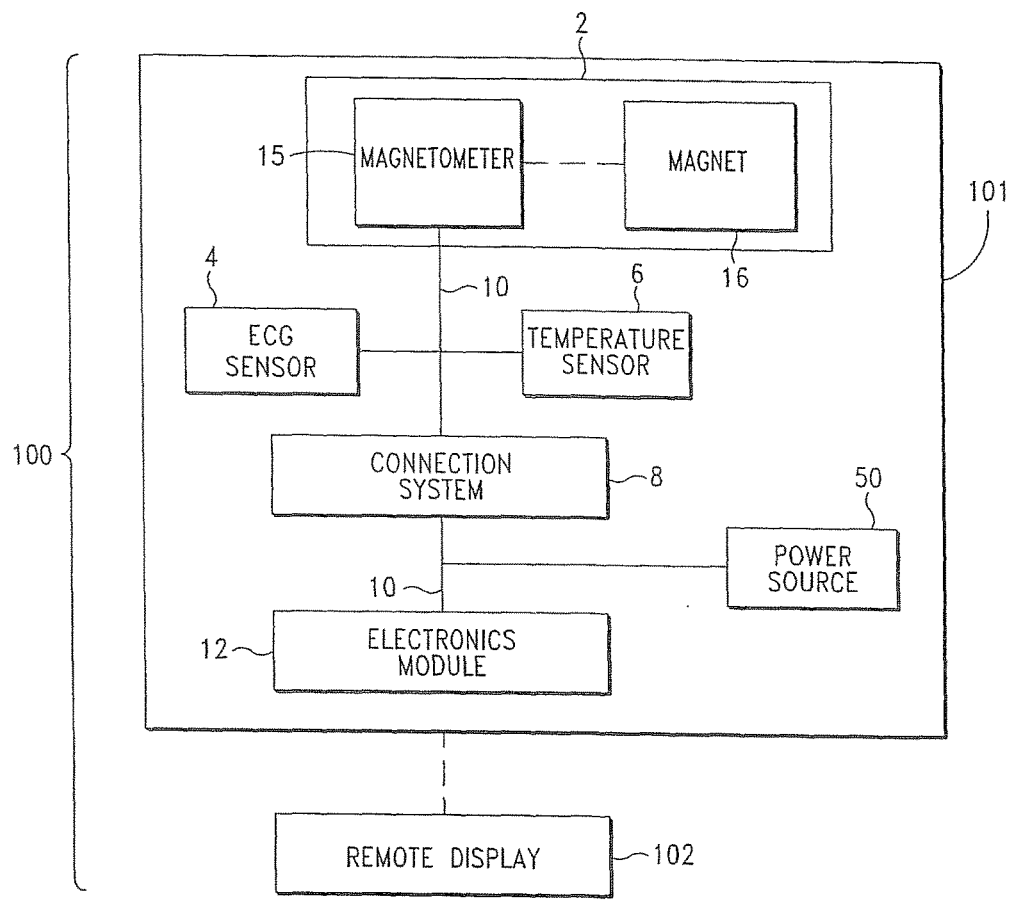
FIG. 1A is a schematic illustration of one embodiment of a respiration monitoring system, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "a sensor signal" includes two or more such signals and the like.

Definitions

The terms "respiratory parameter" and "respiratory characteristic" are used interchangeable herein, and mean and include a characteristic associated with the respiratory system and functioning thereof, including, without limitation, breathing frequency, tidal volume, inspiration volume, expiration volume, minute ventilation, inspiratory breathing time, expiratory breathing time, and flow rates (e.g., rates of change in the chest wall volume).

The terms "respiratory parameter" and "respiratory characteristic" further mean and include parameters associated with ventilation mechanics from synchronous or asynchronous movements of the chest wall compartments.

According to the present invention, flow rates and respiratory accelerations can be determined from a volume signal. Further, numerous inferences regarding ventilation mechanics can be drawn from the degree of asynchrony in movement occurring amongst the discrete compartments that make up the chest wall and the three dimensional movements of the spine.

The terms "respiratory system disorder" and "respiratory disorder" and "adverse respiratory event", as used herein, mean and include any dysfunction of the respiratory system that impedes the normal respiration or ventilation process.

The terms "physiological parameter" and "physiological characteristic", as used herein, mean and include, without limitation, electrical activity of the heart, electrical activity of other muscles, electrical activity of the brain, pulse rate, blood pressure, blood oxygen saturation level, skin temperature, and core temperature.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is understood that although the respiration monitoring systems and associated methods of the invention are described herein in connection with monitoring respiration parameters and characteristics in a human body, the invention is in no way limited to such use. The respiration monitoring systems and associated methods of the invention can also be employed to monitor respiration and other physiological parameters in other mammalian bodies.

The respiration monitoring systems and associated methods of the invention can also be employed in non-medical contexts, such as determining volumes and/or volume changes in extensible bladders used for containing liquids and/or gasses.

As indicated above, the present invention is directed to respiration monitoring systems and associated methods. As discussed in detail herein, in a preferred embodiment of the invention, the respiration monitoring systems of the invention are designed and configured to (i) determine three dimensional displacement of the spine of a subject with respect to the axial displacement of the subject's chest wall, more preferably, three dimensional displacements of the spine with respect to the axial displacements of the chest wall (ii) process the three dimensional anatomical data, i.e. anatomical displacement signals representing same, (iii) determine at least one respiration parameter associated with the subject as a function of the anatomical displacement signals, and (iv) generate at least one respiration parameter signal representing the respiration parameter.

Referring now to FIG. 1A, there is shown a schematic illustration of one embodiment of a respiration monitoring system of the invention. As illustrated in FIG. 1A, the respiration monitoring system 100 preferably includes a respiration detection system 2, signal transmission conductors 10, an electronics module 12 and a power source 50, such as a battery.

Figure 3:
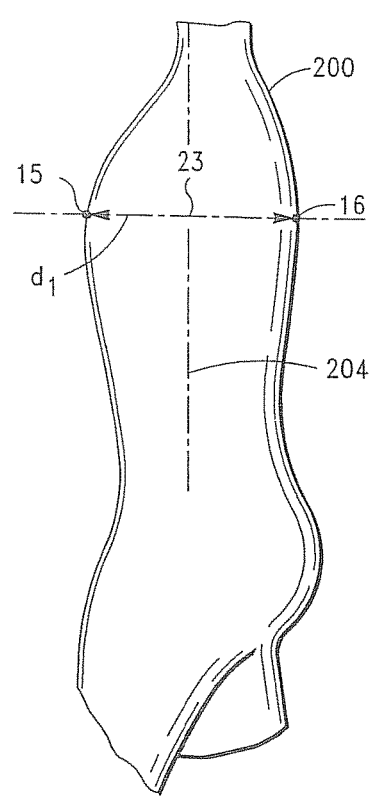
FIG. 3 is a side view of a subject, showing the positioning of the electromagnetic coil and magnet arrangement shown in FIG. 2 on the subject, in accordance with one embodiment of the invention.

In a preferred embodiment of the invention, the respiration detection system 2 comprises at least one electromagnetic coil or magnetometer 15 and at least one magnet 16, which is preferably disposed at a distance $d_2$ from the magnetometer 15 when disposed on a subject (see FIG. 3).

As discussed in detail below, in a preferred embodiment, the respiration detection system 2, i.e. magnetometer 15 and magnet 16, is preferably secured and positioned by a circumferential band 105 (see FIG. 7).

In some embodiments of the invention, the respiration monitoring system 100 further includes one or more additional physiological sensors, such as an ECG sensor 4, temperature sensor 6, and SpO$_2$ sensor (not shown), which are in communication with the signal transmission conductors 10.

According to the invention, the magnet 16 can comprise any device or material that is configured to generate a magnetic field, such as an alternating current (AC) magnetic field and/or a direct current (DC) magnetic field.

In a preferred embodiment, the magnet 16 comprises a conventional permanent magnet that is configured to generate an AC magnetic field.

In a preferred embodiment, the permanent magnet 16 comprises a rare earth magnet, including, but not limited to Neodymium (Nd$_2$Fe$_{14}$B) and Samarium-cobalt (SmCo$_5$).

Figure 1B:
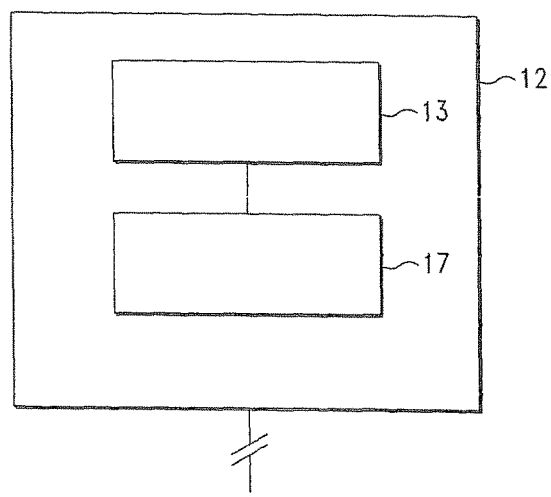
FIG. 1B is a schematic illustration of a respiration monitoring system electronics module, in accordance with the invention.

Referring now to FIG. 1B, the electronics module 12 preferably includes a processing system 13, which is programmed and configured to control the respiration detection system 2 and the function thereof, and the transmission and receipt of signals therefrom.

The module processing system 13 is also preferably programmed and adapted to receive and process anatomical displacement signals from the respiration detection system 2, and determine at least one respiration parameter associated with a monitored subject as a function of the anatomical displacement signals.

Figure 2:
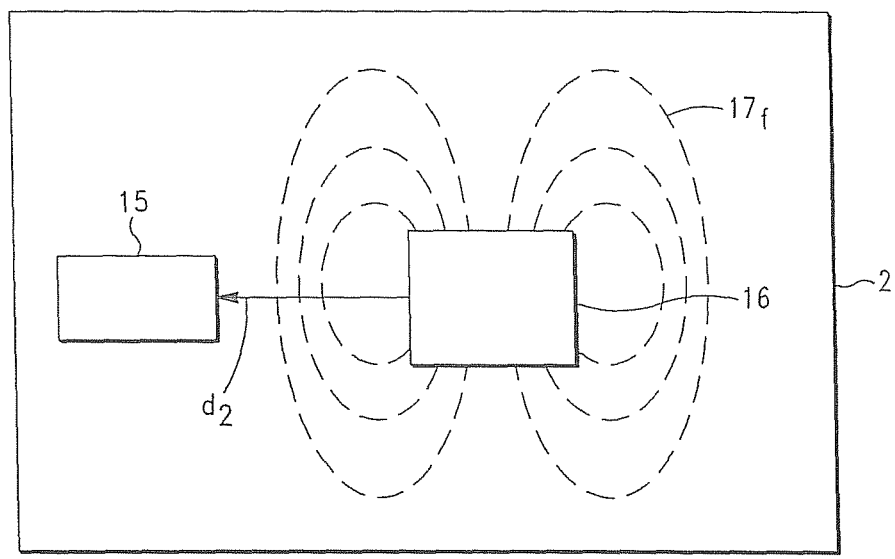
FIG. 2 is a schematic illustration of an electromagnetic coil, i.e. magnetometer, and magnet arrangement, in accordance with one embodiment of the invention.

According to the invention, the anatomical displacement signals transmitted by the respiration detection system 2 represent variations or fluctuations in the strength of the AC magnetic field (denoted "$M_F$" in FIG. 2) that is generated by magnet 16. In a preferred embodiment of the invention, the magnetic field, $M_F$, variations correspond to three dimensional displacement of the spine 204 of a subject 200 (or wearer of a respiration detection system) with respect to axial displacement of the subject's chest wall 202 (see FIGS. 2-4).

In a preferred embodiment of the invention, the module processing system 13 comprises at least one algorithm that is programmed and configured to isolate and process the anatomical displacement signals representing variations in the strength of AC magnetic field, MF, and determine at least one physiological characteristic or parameter, preferably, at least one respiration parameter, as a function of the anatomical displacement signals.

The module processing system is further configured to generate at least one respiration parameter signal representing at least one respiration parameter associated with the monitored subject.

In some embodiments of the invention, the processing algorithm comprises a spectral density estimation algorithm using non-parametric methods, including, without limitation, periodogram, Lomb-Scargle periodogram, Bartlett's method, Welch's method, multitaper, least-squares spectral analysis, non-uniform discreet Fourier transform, singular spectrum analysis, short-time Fourier transform, cross-power method, transfer function estimate and magnitude squared coherence.

In some embodiments, the processing algorithm comprises a spectral density estimation algorithm using parametric methods, including, without limitation, autoregressive model, moving-average model, autoregressive moving average, maximum entropy spectral estimation, Burg's method, covariance method, modified covariance method and Yule-Walker method.

In some embodiments, the processing algorithm comprises a frequency domain algorithm, including, without limitation, a Fourier series algorithm, Fourier transform algorithm, Laplace transform algorithm, Z transform algorithm and wavelet transform algorithm.

In a preferred embodiment of the invention, the processing algorithm comprises a Fourier transform algorithm.

In a preferred embodiment of the invention, the electronics module 12 further includes a data transmission system 17 comprising a transmitter that is programmed and configured to transmit the respiration parameter signals to a signal receiving device. In a preferred embodiment, the signal receiving device comprises a remote signal receiving device, e.g., a base module or a hand-held electronic device, such as a smart phone, tablet, computer, etc.

In some embodiments, the transmission system 17 is programmed and configured to wirelessly transmit the respiration parameter signals via optical or capacitive signal transmission means including, but not limited to, Wi-Fi, Bluetooth, Bluetooth Low Energy, near field communication (NFC), radio frequency identification (RFID) and Zigbee.

As further illustrated in FIG. 1A, the respiration monitoring system 100 further includes a connection system 8, which facilitates connection and thereby, signal communication by and between the respiration detection system 2, signal transmission conductors 10, electronics module 12 and additional physiological sensors (if employed), and a remote display unit 102.

In a preferred embodiment, the remote display unit 102 includes a receiver that is programmed and configured to receive the physiological parameter signals generated by the processing system 13. The remote display 102 is also programmed to display respiration parameters associated with the respiration parameter signals on the display unit.

Referring now to FIGS. 1-7, an exemplary embodiment of a physiological monitoring system of the invention will be described in detail.

As indicated above, in a preferred embodiment of the invention, the respiration monitoring system 100 shown in FIG. 1A is designed and configured to (i) determine three dimensional displacement of the spine (represented by dashed line denoted 204 in FIG. 3) of a subject 200 with respect to the axial displacement of the subject's chest wall 202, (ii) process the three dimensional anatomical data, i.e. anatomical displacement signals representing same, (iii) determine at least one respiration parameter associated with the subject as a function of the anatomical displacement signals, and (iv) generate at least one respiration parameter signal representing the respiration parameter.

In some embodiments, the respiration monitoring system 100 is further adapted to monitor one or more additional physiological characteristics associated with the monitored subject.

Figure 6:
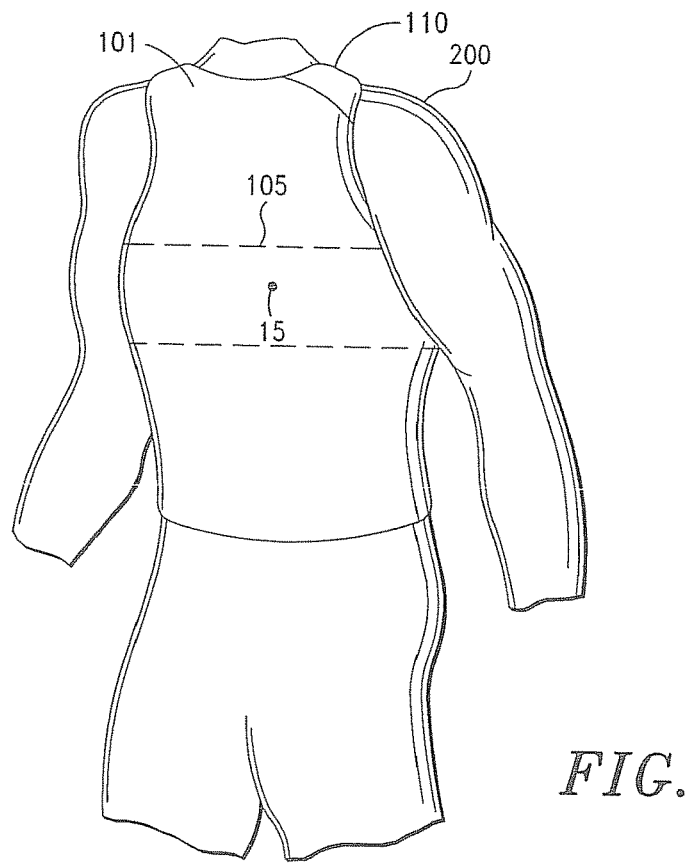
FIG. 6 is a perspective view of one embodiment of a wearable respiration monitoring system on a subject, in accordance with the invention.
Figure 7:
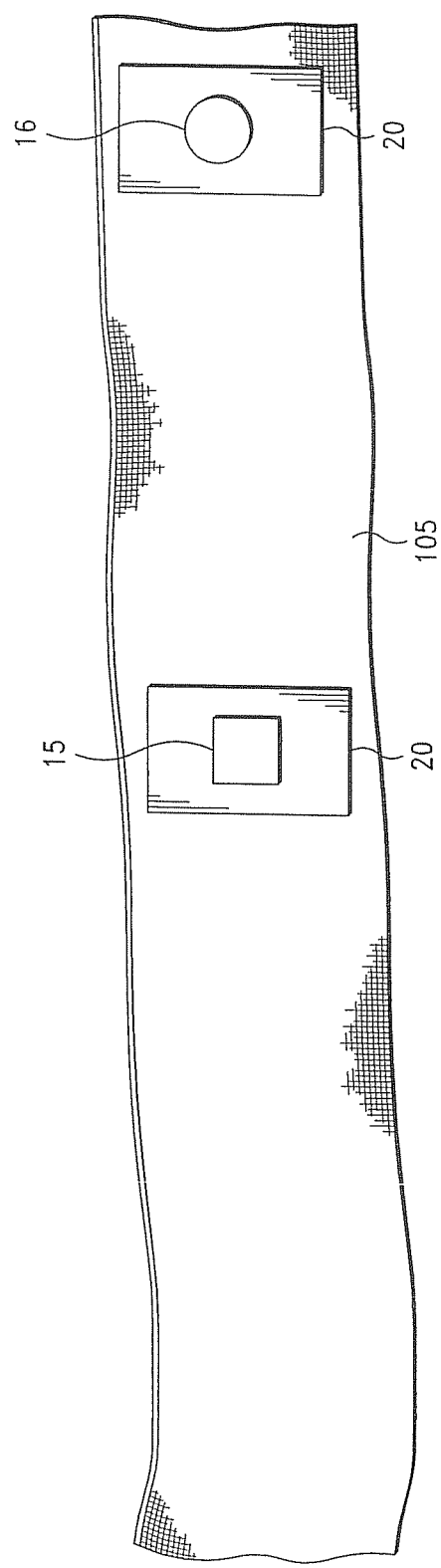
FIG. 7 is a top plan view of one embodiment of a circumferential band having a respiration detection system associated therewith, in accordance with the invention.

Referring now to FIGS. 6 and 7, as indicated above, in a preferred embodiment of the invention, the respiration monitoring system 100 includes wearable garment 101. In a preferred embodiment, the garment 101 includes circumferential band 105, which is attached an interior portion of the garment 101.

According to the invention, the garment 101 can comprise various conventional fabrics having fibers of variable loft and thickness. In some embodiments of the invention, the garment comprises a form fitting garment constructed of Lycra® or like material.

In some embodiments of the invention, the circumferential band 105 comprises a conductive fabric.

In some embodiments of the invention, at least one of the shoulder portions 110 of the garment 101 comprises a two-piece portion, i.e. an over-lapping strap configuration, to facilitate easy placement of the garment 101 on a wearer, e.g., elderly user. In the noted embodiments, the two-piece portion includes a conventional Velcro® system or hooks or snaps to secure the ends of the over-lapping strap after the garment 101 is positioned on the wearer's body.

In a preferred embodiment of the invention, the garment 101 includes at least one opening, which is preferably disposed in the front of the garment 101, for releasable attachment of electronic components, e.g. the electronics module 12 (discussed below), diagnostic devices, etc., to the garment band 105.

As indicated above and discussed in detail below, the garment band 105 is also configured to receive and secure the respiration detection system 2 (see FIG. 7).

As also indicated above, the respiration detection system 2 preferably comprises at least one magnetometer 15 and at least one magnet 16.

According to the invention, the respiration detection system 2 can also comprise a plurality of magnetometers, such as disclosed in Co-Pending application Ser. No. 13/854,280, and associated magnets.

In some embodiments of the invention, the band 105 includes pockets 20 that are configured to removeably receive and, hence, position the respiration detection system 2, i.e. magnetometer 15 and magnet 16 (see FIG. 7). In some embodiments, the magnetometer 15 and/or magnet 16 is permanently attached to the band 105.

As indicated above, in a preferred embodiment of the invention, the respiration detection system 2 is designed and configured to determine three dimensional displacements of the spine 204 of a subject (or wearer of a monitoring system) 200 with respect to the axial displacements of the subject's chest wall 202.

In a preferred embodiment, the detection system magnetometer 15 is configured (and positioned) to detect and measure variations in strength of the AC magnetic field, $M_F$, which is generated by magnet 16. As indicated above, according to the invention, variations in the strength of the AC magnetic field, $M_F$, correspond to three dimensional displacements of the spine 204 of a wearer 200 of the respiration monitoring system 100 with respect to axial displacements of the wearer's chest wall 202.

According to the invention, the strength variations in AC magnetic field, $M_F$, detected by the magnetometer 15 are proportional to the square of the distance $d_2$ from the magnet 16. Thus, changes in distance $d_2$ on the order of millimeters can cause a dramatic change in the strength variation of the AC magnetic field, MF.

According to the invention, differences in distance $d_2$ in the range of 3-5 mm can be employed to effectively detect variations in the strength of AC magnetic field, $M_F$.

As indicated above, in a preferred embodiment, the processing system 13 includes a Fourier transform algorithm that is configured to process the anatomical displacement signals and determine at least one respiration parameter, such as breathing frequency, of a monitored subject, as a function of the respiration detection system signals.

In a preferred embodiment, the respiration parameter that is reflected by an anatomical displacement signal is based, in significant part, on the distance $d_2$ between the magnetometer 15 and the magnet 16. According to the invention, abrupt movements, such as movements made by a coughing subject, can thus be readily detected and measured in real time.

In a preferred embodiment, the magnetometer 15 is configured to detect and measure low frequency variations in AC magnetic field, $M_F$, strength over time. In some embodiments, frequencies in the range of 0.05 to 1 Hertz (Hz) in the AC magnetic field, $M_F$, of magnet 16 reflect approximately 3 to 60 breaths per minute.

Figure 4:
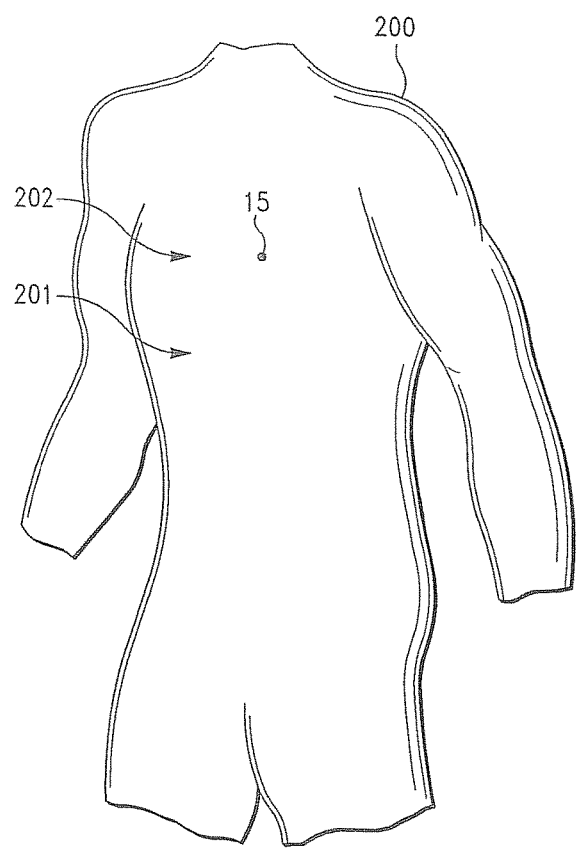
FIG. 4 is a perspective view of the subject shown in FIG. 3, showing the position of an electromagnetic coil on the front of the subject, in accordance with one embodiment of the invention.
Figure 5:
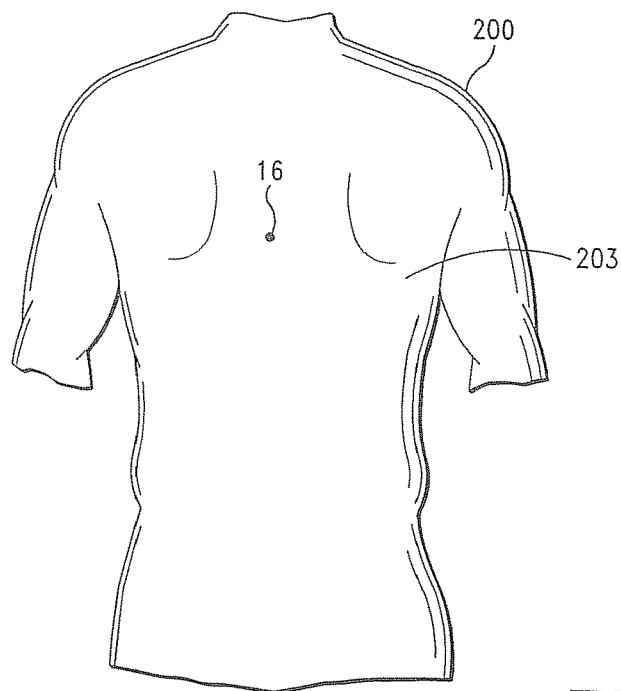
FIG. 5 is a plan view of the back of the subject shown in FIG. 3, showing the position of a magnet thereon, in accordance with one embodiment of the invention.

As indicated above and illustrated in FIG. 3-5, the magnetometer 15 and magnet 16 are preferably disposed in-plane (denoted by line "23"). In some embodiments, magnetometer 15 is disposed on the front of the subject 200 proximate the subject's xyphoid process, i.e. the bottom tip of the sternum, and magnet 16 is disposed on the back 203 of the subject 200 proximate the same axial position.

In some embodiments, magnet 16 is disposed on the front of the subject 200 proximate the subject's xyphoid process and magnetometer 15 is disposed on the back 203 of the subject 200 proximate the same axial position.

As also indicated above and shown in FIG. 1B, in a preferred embodiment of the invention, the electronics module 12 includes a processing system 13 that includes programs, parameters, instructions and at least one associated algorithm to control the respiration detection system 2 and the function thereof, and the transmission and receipt of signals therefrom, as well as the data transmission system 17.

In a preferred embodiment, the module processing system 13 is programmed and configured to detect and process the anatomical displacement signals and, hence, changes in spaced distance between the magnetometer 15 and magnet 16, and determine at least one respiration parameter, more preferably, a plurality of respiratory parameters of the monitored subject 200 as a function of the anatomical displacement signals.

In some embodiments of the invention, the module processing system 13 (or the remote display unit 102, discussed below) also includes a "rules set" that includes a rule in which an alert signal is transmitted if the anatomical displacement signals indicate that a respiratory or other physiological parameter that is being monitored is outside a predetermined range.

In some embodiments, the module processing system 13 is programmed and configured to detect respiratory abnormalities, such as asthma or COPD, based on at least one respiratory parameter.

As stated above, in a preferred embodiment, the module data transmission system 17 is programmed and configured to wirelessly transmit respiration parameter signals processed by the module processing system 13 to a remote signal receiving device, such as a base module or a hand-held electronic device, via one of the aforementioned via optical or capacitive signal transmission means.

According to the invention, the module 12 can further includes a GPS or other position detection subsystem, and/or a motion detector, such as an accelerometer. The module can further include separate display means.

Figure 8:
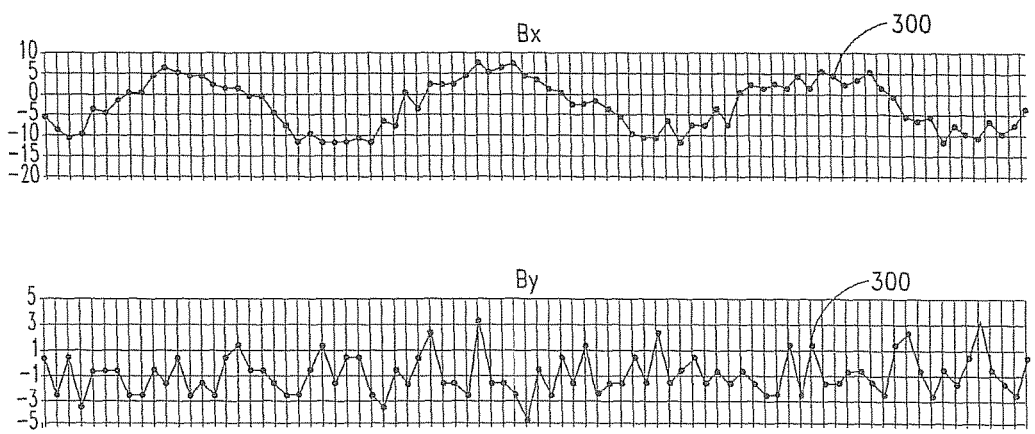
FIGS. 8-9 are graphical illustrations representing a subject's breathing patterns as a function of time, as provided by a wearable respiration monitoring system, in accordance with one embodiment of the invention.
Figure 9:
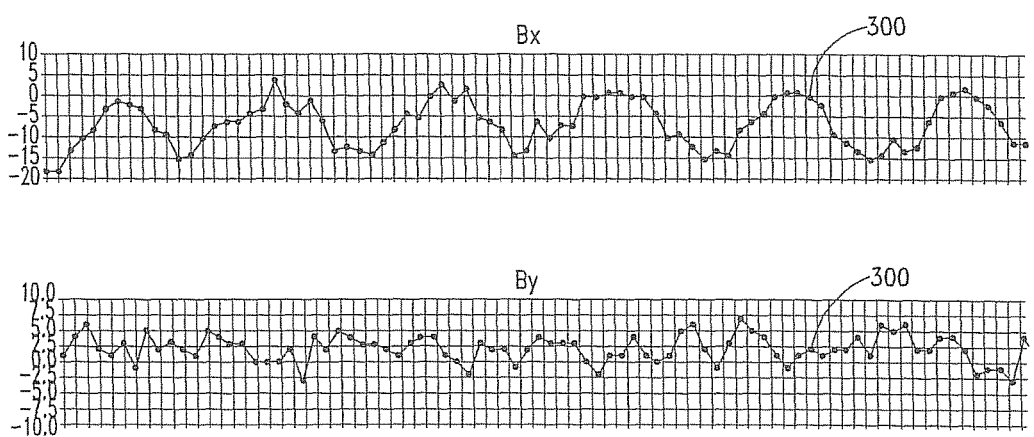

Referring now to FIGS. 8 and 9, there are shown graphical representations of a respiratory parameters, i.e. breathing frequency, of a subject determined by the respiration monitoring system 100 employed in wearable garment 101, where FIG. 8 reflects a relatively slow respiration frequency of 20 breaths per minute and FIG. 9 reflects a relatively fast respiration frequency of 39 breaths per minute.

As illustrated in FIGS. 8 and 9, the graphs comprise data points 300, where each data point 300 represents the relative AC magnetic field strength, $M_{FS}$, at a given time over 0.1 second increments, as provided via Fourier analysis.

According to the invention, the relative AC magnetic field strength comprises relative magnetic field strength "Rel $M_{FS}$" in three dimensions, i.e. (Rel $M_{FS}$)$_x$, (Rel $M_{FS}$)$_y$, and (Rel $M_{FS}$)$_z$.

As will readily be appreciated by one having ordinary skill in the art, the present invention provides numerous advantages compared to prior art methods and systems for monitoring and/or detecting physiological characteristics. Among the advantages are the following:

The provision of a respiration monitoring system and method that accurately (i) monitors and detects three dimensional displacement of the spine with respect to the axial displacements of the chest wall and (ii) determines anatomical and physiological information; particularly, respiratory parameters, associated with the monitored subject as a function of signals reflecting the noted anatomical displacements.

The provision of a respiration monitoring system and method that accurately measures multiple physiological characteristics associated with a user or wearer, while minimizing inference from external sources, such as electromagnetic radiation.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method of detecting a respiration parameter of a subject, said subject comprising a spine and xyphoid process of the sternum, comprising the steps of:

providing a wearable respiration monitoring system that is configured to be removably positioned on a subject and cover at least a chest region and an upper back region of said subject when positioned on said subject, said wearable respiration monitoring system comprising a respiration detection system comprising a power source, electronics module, permanent rare earth magnet and an electromagnetic coil, said electromagnetic coil being in communication with said rare earth magnet, said power source and electromagnetic coil being in communication with said electronics module, said rare earth magnet being adapted to generate a three-dimensional alternating current (AC) magnetic field comprising a variable strength in at least one of said AC magnetic field dimensions, said electromagnetic coil being adapted to receive said AC magnetic field, when said wearable respiration monitoring system is positioned on said subject and said rare earth magnet and said electromagnetic coil are in axial alignment, and detect said variable strength in said at least one of said AC magnetic field dimensions, said variable strength in at least one of said AC magnetic field dimensions representing a variation in distance between said rare earth magnet and said electromagnetic coil and, thereby, an anatomical displacement of said subject's xyphoid process relative to said subject's spine, during a respiration cycle of said subject, said electromagnetic coil being further adapted to generate at least one anatomical displacement signal as a function of said variable strength in said at least one AC magnetic field dimension, said electronics module being configured to receive said at least one anatomical displacement signal from said electromagnetic coil and determine at least one respiration parameter of said subject as a function of said at least one anatomical displacement signal;

positioning said wearable respiration monitoring system on a first subject, wherein said wearable respiration monitoring system is disposed proximate said first subject's xyphoid process and spine;

initiating said respiration detection system with said electronic module of said wearable respiration monitoring system;

detecting a first variable strength in said at least one of said AC magnetic fields generated by said rare earth magnet with said electromagnetic coil;

generating a first anatomical displacement signal as a function of said first variable strength in said at least one AC magnetic field dimension with said electromagnetic coil; and determining a first respiration parameter of said first subject as a function of said first anatomical displacement signal with said electronics module of said wearable respiration monitoring system.

2. A method of detecting a respiration parameter of a subject, said subject comprising a spine and xyphoid process of the sternum, comprising the steps of:

providing a wearable respiration monitoring system that is configured to be removably positioned on a subject and cover at least a chest region and an upper back region of said subject when positioned on said subject, said wearable respiration monitoring system comprising a respiration detection system comprising a power source, electronics module, permanent rare earth magnet and an electromagnetic coil, said electromagnetic coil being in communication with said rare earth magnet, said power source and electromagnetic coil being in communication with said electronics module, said rare earth magnet being adapted to generate a three-dimensional alternating current (AC) magnetic field comprising a variable strength in said AC magnetic field dimensions, said electromagnetic coil being adapted to receive said AC magnetic field, when said wearable respiration monitoring system is positioned on said subject and said rare earth magnet and said electromagnetic coil are in axial alignment, and detect said variable strength in said AC magnetic field dimensions, said variable strength in said AC magnetic field dimensions representing variations in distance between said rare earth magnet and said electromagnetic coil in said AC magnetic field dimensions, said electromagnetic coil being further adapted to generate a plurality of anatomical displacement signals as a function of said variable strengths in said AC magnetic field dimensions, said electronics module being configured to receive said plurality of anatomical displacement signals from said electromagnetic coil and determine at least one respiration parameter of said subject as a function of said plurality of anatomical displacement signals;

positioning said wearable respiration monitoring system on a first subject, wherein said wearable respiration monitoring system is disposed proximate said first subject's xyphoid process and spine;

initiating said respiration detection system with said electronic module of said wearable respiration monitoring system;

detecting a first plurality of variable strengths in said AC magnetic fields generated by said rare earth magnet with said electromagnetic coil;

generating a first plurality of anatomical displacement signals as a function of said first plurality of variable strengths in said AC magnetic fields with said electromagnetic coil; and determining at least a first respiration parameter of said first subject as a function of said first plurality of anatomical displacement signals with said electronics module of said wearable respiration monitoring system.

\* \* \* \* \*